(12) United States Patent
Zhang et al.

(10) Patent No.: US 10,429,411 B2
(45) Date of Patent: Oct. 1, 2019

(54) NEAR FIELD SCANNING PROBE MICROSCOPE, PROBE FOR SCANNING PROBE MICROSCOPE, AND SAMPLE OBSERVATION METHOD

(71) Applicant: Hitachi, Ltd., Chiyoda-ku, Tokyo (JP)

(72) Inventors: Kaifeng Zhang, Tokyo (JP); Shinichi Taniguchi, Tokyo (JP)

(73) Assignee: Hitachi, Ltd., Tokyo (JP)

( * ) Notice: Subject to any disclaimer, the term of this patent is extended or adjusted under 35 U.S.C. 154(b) by 0 days.

(21) Appl. No.: 15/928,790

(22) Filed: Mar. 22, 2018

(65) Prior Publication Data

US 2018/0372776 A1   Dec. 27, 2018

(30) Foreign Application Priority Data

Jun. 21, 2017   (JP) ................................. 2017-121232

(51) Int. Cl.
    *G01Q 60/18*   (2010.01)
    *G01Q 60/22*   (2010.01)
    (Continued)

(52) U.S. Cl.
    CPC .............. *G01Q 60/18* (2013.01); *B82Y 15/00* (2013.01); *B82Y 30/00* (2013.01); *B82Y 40/00* (2013.01);
    (Continued)

(58) Field of Classification Search
    CPC ........ G01Q 60/18; G01Q 60/20; G01Q 60/22; G01Q 70/08; G01Q 70/16; G01Q 70/18
    (Continued)

(56) References Cited

U.S. PATENT DOCUMENTS

2003/0038223 A1* 2/2003 Fleming .................. F16C 11/12
                                                          248/564
2003/0038233 A1* 2/2003 Inoue ..................... B82Y 20/00
                                                          250/234

(Continued)

FOREIGN PATENT DOCUMENTS

JP        2008-281530 A     11/2008

OTHER PUBLICATIONS

Inouye et al., "Near-field scanning optical microscope with a metallic probe tip", Optics Letters, Feb. 1, 1994, pp. 159-161, vol. 19, No. 3.

(Continued)

*Primary Examiner* — Jason L McCormack
(74) *Attorney, Agent, or Firm* — Crowell & Moring LLP

(57) ABSTRACT

A near-field scanning probe includes: a measurement probe that relatively scans a test sample; an excitation light irradiation system; a near-field light generation system that generates near-field light in a region including the measurement probe in response to irradiation with excitation light from the excitation light irradiation system; and a scattered light detection system that detects Rayleigh scattering and Ramen scattered light of the near-field light from the sample, generated between the measurement probe and the sample, and the near-field scanning probe is characterized in that the near-field light generation system includes a cantilever with a chip coated with a noble metal, and a tip of the chip is provided with a thin wire group including a plurality of carbon nanowires with a noble metal provided at ends thereof.

16 Claims, 13 Drawing Sheets

(51) Int. Cl.
*G01Q 70/12* (2010.01)
*B82Y 15/00* (2011.01)
*B82Y 30/00* (2011.01)
*B82Y 40/00* (2011.01)
*G01N 21/65* (2006.01)
*C01B 32/18* (2017.01)

(52) U.S. Cl.
CPC ............ *C01B 32/18* (2017.08); *G01N 21/65* (2013.01); *G01Q 60/22* (2013.01); *G01Q 70/12* (2013.01); *G01N 2021/656* (2013.01)

(58) Field of Classification Search
USPC ................ 850/21, 30, 31, 32, 52, 56, 59, 60
See application file for complete search history.

(56) References Cited

U.S. PATENT DOCUMENTS

| 2005/0250243 | A1 | 11/2005 | Bonnell et al. |
| 2008/0286563 | A1 | 11/2008 | Konakahara |
| 2010/0141939 | A1* | 6/2010 | Zhan ........................ G01J 3/02 356/301 |
| 2015/0355227 | A1* | 12/2015 | Gluckstad .............. G01Q 60/22 850/32 |
| 2015/0377922 | A1 | 12/2015 | Nakata et al. |

OTHER PUBLICATIONS

Hayazawa et al., "Detection and characterization of longitudinal field for tip-enhanced Raman spectroscopy", Applied Physics Letters, Dec. 20, 2004, pp. 6238-6241, vol. 85, No. 25, American Institute of Physics.

Bekarevich et al., "Refilling of carbon nanotube cartridges for 3D nanomanufacturing", Nanoscale, The Royal Society of Chemistry, 2016, pp. 7217-7223, vol. 8.

Office Action of corresponding U.S. Appl. No. 16/520,571 dated Aug. 13, 2019 (16 pages).

* cited by examiner

NEAR FIELD SCANNING PROBE MICROSCOPE, PROBE FOR SCANNING PROBE MICROSCOPE, AND SAMPLE OBSERVATION METHOD

CLAIM OF PRIORITY

This application claims the priority from the Japanese Patent Application No. 2017-121232 filed on Jun. 21, 2017, the content of which is incorporated herein by reference into this application.

BACKGROUND

Technical Field

The present invention relates to, for example, a near-field scanning probe microscope, a probe for a scanning probe microscope, and a sample observation method.

Related Art

JP 2008-281530 A describes "a probe for surface enhanced vibration spectroscopic analysis, characterized in that the probe is formed on a cantilever, a plurality of metal fine particles is dispersed inside the probe, and the plurality of metal fine particles is exposed at the surface of the probe".

SUMMARY

According to the technology described in JP 2008-281530 A, first, the minimum diameter of noble metal particles that can be produced is larger than 10 nm (nanometers) and actually often 30 nm or more on average, and it is thus difficult to further improve the spatial resolution which depends on the particle size. In addition, the use of a macroscopic film formation approach causes the noble metal particles to vary in size, causes gaps in spatial position of fine particle, and the like at the time of production, and during the measurement with the use of an in-depth probe, causes changes in, due to contact with a sample, the shapes of the noble metal particles exposed at the end of the in-depth probe, and the like, and it is not appropriate for consider the measurement reproducibility of the in-depth probe to be considered high.

An object of the present invention is to provide a near-field scanning probe microscope, a probe for a scanning probe microscope, and a sample observation method, which can improve spatial resolution and reproducibility for measurement.

The present application encompasses more than one means for at least partially solving the problems mentioned above, and an example of the means will be given as follows. In order to solve the problems mentioned above, a near-field scanning probe microscope according to an aspect of the present invention includes: a measurement probe that relatively scans a test sample; an excitation light irradiation system; a near-field light generation system that generates near-field light in a region including the measurement probe in response to irradiation with excitation light from the excitation light irradiation system; and a scattered light detection system that detects Rayleigh scattering and Ramen scattered light of the near-field light from the sample, generated between the measurement probe and the sample, and the near-field scanning probe is characterized in that the near-field light generation system includes a cantilever with a chip coated with a noble metal, and a tip of the chip is provided with a thin wire group including a plurality of carbon nanowires with a noble metal provided at ends thereof.

According to the present invention, a near-field scanning probe microscope, a probe for a scanning probe microscope, and a sample observation method can be provided which can improve spatial resolution and reproducibility for measurement. Objects, configurations, and advantageous effects other than the foregoing will be evident from the following description of embodiments.

DETAILED DESCRIPTION

Figure 1:
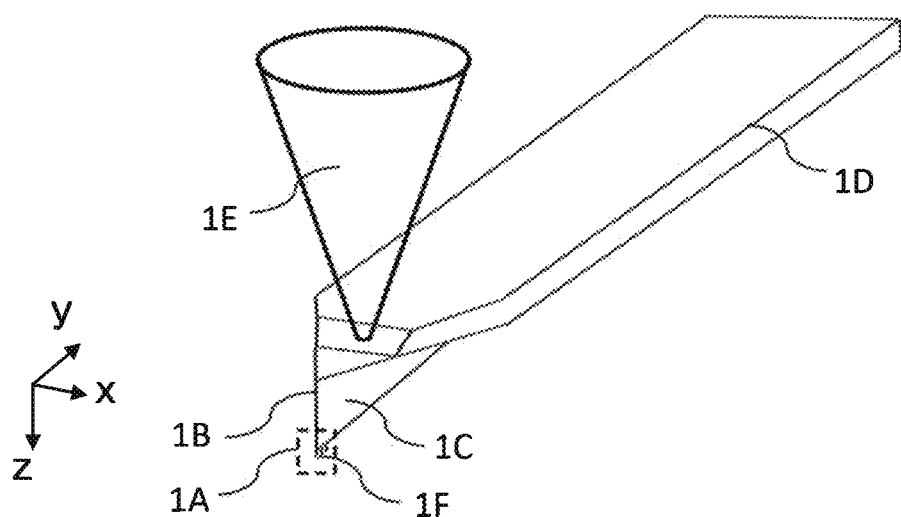
FIG. 1 is a perspective view illustrating an example of a cantilever and an in-depth probe group fixed to a tip of the cantilever according to a first embodiment.

As a means for measuring optical properties of a sample surface and physical property information thereon at high resolution, a near-field scanning microscope (SNOM: Scanning Near-field Optical microscope) is known (for example, see Optics Letters, Vol. 19, pp. 159-161 (1994)). In recent years, a spectrometer that allows for nanoresolution Raman spectrometry through the use of a local enhancement effect of near-field light has been developed as one application of the SNOM technology (for example, see "Detection and characterization of longitudinal field for tip-enhanced Raman spectroscopy" Appl. Phys. Lett. 85, 6239 (2004)). In addition, recently, technologies of filling carbon wires with gold has been established, such as CNT (Carbon Nano Tube) (for example, see "Refilling of carbon nanotube cartridges for 3D nanomanufacturing" Nanoscale 8.13 (2016): 7217-7223).

The near-field scanning probe microscope according to the present invention can further improve the spatial resolution of AFM-Raman (a composite system of a microscopic Raman spectrometer and an atomic force microscope (Atomic Force Microscope)), because it is possible to achieve the sizes of noble metal particles included in carbon wires so as to be less than 10 nm in transverse diameter. In addition, the sizes of the noble metal particles mentioned above are equal to the inside diameters of the carbon wires, thus making it easier to control the sizes of the noble metal particles. In addition, it is possible to arrange the carbon wires in predetermined locations, thereby making it easier to arrange and manage the noble metal particles. Furthermore, because the noble metal particles are not exposed, and because the carbon wires are high in strength, the change in the shape of the noble metal at the end of the in-depth probe can be kept small, thus making it possible to make the life of the in-depth probe longer. As a result, the measurement reproducibility of, in particular, AFM-Raman can be further improved.

First Embodiment

A first embodiment according to the present invention will be described with reference to FIGS. 1 to 5. It is to be noted that in all of the figures for explaining not only the first embodiment but also embodiments, like members are denoted by like numerical references in principle, and repeated descriptions thereof may be omitted in some cases. In addition, in the following embodiments, obviously, the constituent elements (including element steps) are not necessarily to be considered essential, e.g., unless otherwise expressly provided, and unless considered clearly essential in principle. In addition, obviously, the phrases of "being composed of A", "being made from A", "having A", and "including A" are not to be considered to exclude other elements, e.g., unless only the element is expressly provided herein otherwise. Likewise, in the following embodiments, the reference to the shapes, positional relationships, and the like of the constituent elements and the like is intended to encompass equivalents substantially approximate or similar to the shapes and the like, e.g., unless otherwise expressly provided, and unless considered clear in principle.

FIG. 1 is a perspective view illustrating an example of a cantilever and an in-depth probe group fixed to a tip of the cantilever according to the first embodiment. The Si cantilever 1D includes an arm and a triangular pyramid chip 1B. The chip 1B is coated with a gold (Au) thin film 1C, and subjected to FIB processing. Furthermore, a carbon nanowire group 1A filled with gold (for example, the carbon nanowire is a CNT: Carbon Nano Tube) is fixed to a tip of the chip 1B. The carbon nanowire group 1A (in-depth probe group) is formed by fixing a plurality of carbon nanowires filled with gold in a predetermined arrangement near the tip of the chip 1B.

In this regard, the material of the chip 1B is suitably Si (silicon), but not limited thereto, and may be $SiO_2$ (silicon dioxide), $Si_3N_4$ (silicon nitride) or the like, as long as the material transmits laser light of a specific wavelength. In addition, the gold thin film 1C may be a film of any other metal (including aluminum (Al), silver (Ag)) material.

Figure 2:
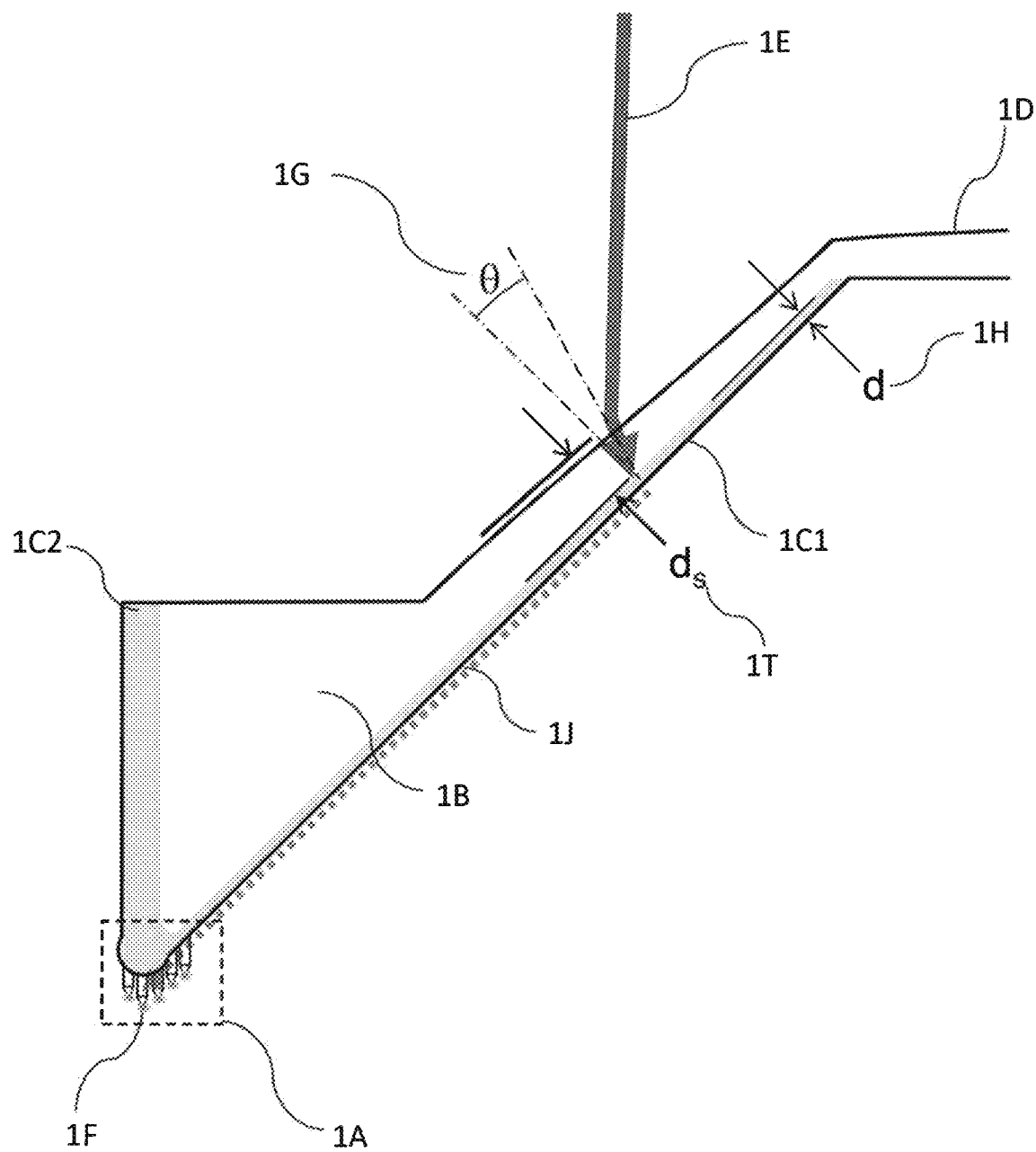
FIG. 2 is a side view illustrating an example of a part of the cantilever, a chip, the in-depth probe group fixed to a tip of the chip, and a light path of excitation laser light in the chip according to the first embodiment.

The arm of the Si cantilever 1D has, as shown in FIG. 2, a light entrance slope formed to allow excitation laser light 1E (energy with a predetermined wavelength) to be incident at a predetermined angle.

FIG. 2 is a side view illustrating an example of a part of the cantilever, the chip coated with gold, the in-depth probe group fixed to the tip of the chip, and a light path of excitation laser light in the chip according to the first embodiment. As shown in FIG. 2, the upper end of the chip 1B is subjected to FIB processing. The Si cantilever 1D is used in a way that irradiates, with the excitation laser light 1E, the light entrance slope contiguous to the plane of a rear gold thin film 1C2 of the chip 1B. The thickness $d_s$ 1T of the Si layer onto which the excitation laser light 1E is made incident is increased in thickness in closer to the tip of the chip of the Si cantilever 1D. As shown in FIG. 2, the thickness $d_s$ 1T of the Si layer is adapted to be approximately 250 nm around the middle. It is to be noted that the thickness $d_s$ 1T of the Si layer is not limited to the case where the thickness is increased in closer to the tip of the chip, but may be constant in thickness.

In use, the near-field scanning probe microscope makes the excitation laser light 1E with various wavelengths from the back side (the side opposed to the side provided with the carbon nanowire group 1A) of the Si cantilever 1D. In this regard, FIG. 3 shows therein a graph obtained by plotting the relationship between the incidence angle θ1G of the excitation laser light 1E and the reflected light intensity from the incident point, that is, the reflectance at the gold/Si interface.

Figure 3:
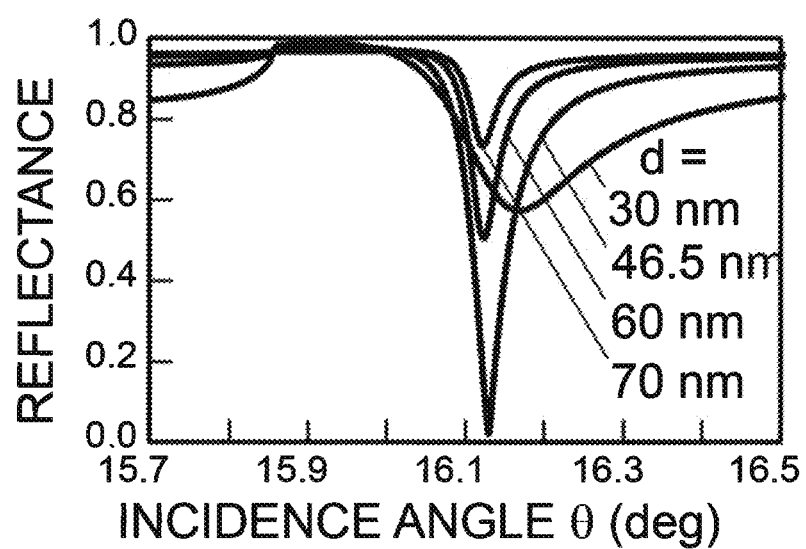
FIG. 3 is a graph showing the relationship (plasmon resonance curve) between the incidence angle and surface reflectance of the excitation laser light according to the first embodiment.

FIG. 3 is a graph showing the relationship (plasmon resonance curve) between the incidence angle and surface reflectance of the excitation laser light according to the first embodiment. It is to be noted that "d" in FIG. 3 corresponds to the film thickness 1H of the gold thin film 1C which blocks laser light of 850 nm in wavelength, as shown in FIG. 2. From FIG. 3, when the excitation laser light 1F is 850 nm in wavelength, strong plasmon resonance is generated at the gold/Si interface at the incidence angle θ around 16.12°, thereby exciting surface plasmon (collective oscillation of free electrons of gold) 1J, and the surface plasmon 1J propagates toward the tip of the chip 1B coated with gold (Au).

In addition, referring to FIG. 3, the reflectance is minimum when the thickness d of the gold thin film 1C1 is 46.5 nm. More specifically, the film thickness d of 46.5 nm can maximize the plasmon resonance. However, the incidence angle varies depending on the excitation wavelength and the type of the metal deposited on the Si. In accordance with the foregoing, the surface plasmon 1J corresponding to the excitation wavelength propagates toward the tip of the chip 1B coated with gold.

Figure 4:
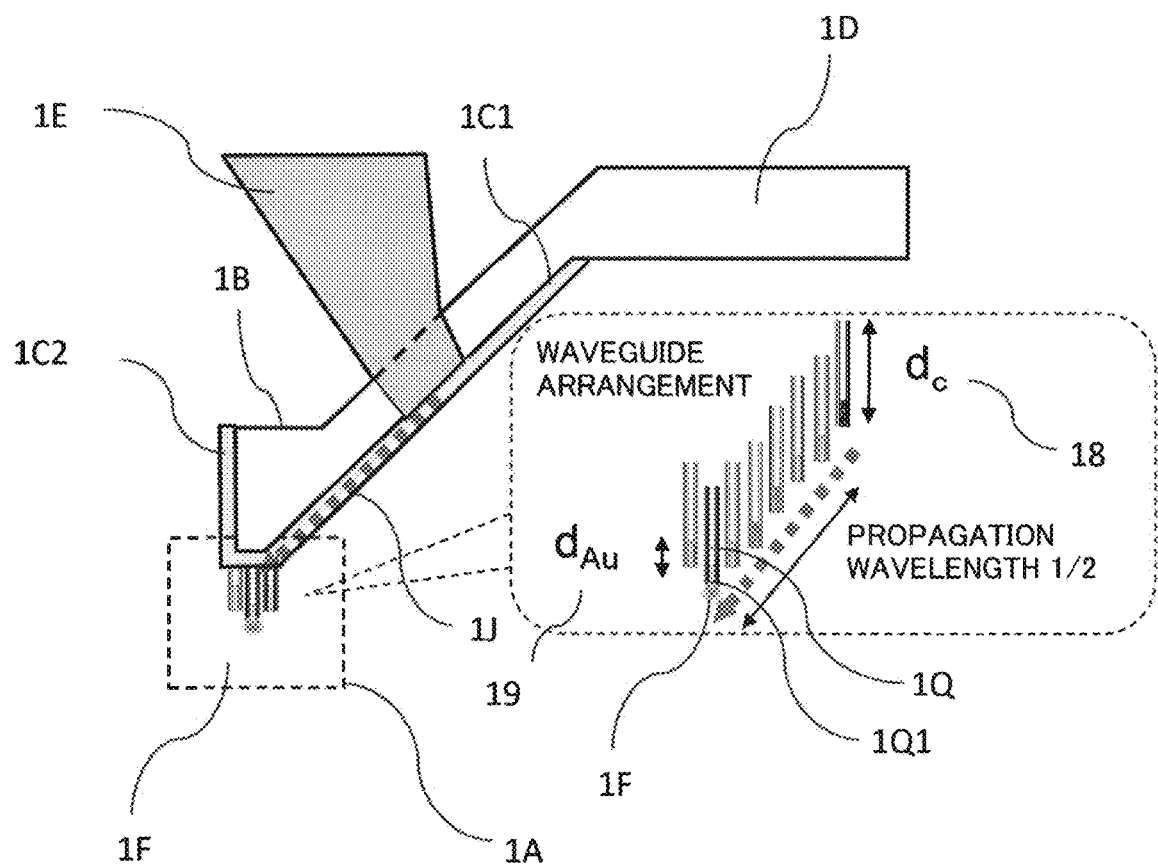
FIG. 4 is a diagram illustrating an arrangement example of a carbon wire probe group according to the first embodiment.

FIG. 4 is a diagram illustrating an arrangement example of the carbon nanowire (in-depth probe) group according to the first embodiment. The tip part of the carbon nanowire group 1A filled with gold is located near the tip of the chip 1B. In order to achieve a measurement resolution, one carbon nanowire of the carbon nanowire group 1A, disposed at the lowermost end, serves as a main carbon nanowire 1Q. The main carbon nanowire 1Q determines the measurement resolution, for use in closest to a sample. Near the main carbon nanowire 1Q, a plurality of auxiliary carbon nanowires is provided in a predetermined arrangement (for example, linearly) in the plasmon propagation direction (the direction from the point where the excitation laser light 1E is made incident toward the tip of the chip 1B), so as to act as an antenna (waveguide).

The carbon nanowires and main carbon nanowire 1Q filled with gold can be fixed to the tip of the chip 1B in a predetermined location by a method such as sputtering. The gold particles filling the end of the main carbon nanowire 1Q propagate, as an antenna, more plasmon energy to a gold filled part 1Q1 of the main carbon nanowire disposed at the lowermost end of the carbon nanowire group 1A. Near-field light 1F for measurement is generated at the gold filled part 1Q1 of the main carbon nanowire 1Q.

The length $d_c$ 18 of the main carbon nanowire 1Q, is about 50 to 100 nm. The filling gold particles are vertically long, and the length $d_{Au}$ 19 of the gold particle is 10 to 30 nm. The transverse diameter corresponds to the inside diameter of the carbon nanowire, which is 5 to 10 nm. The effective size of the near field obtained by electric field concentration corresponds to 1 to 2 times as large as the diameter of the gold particle, thus allowing for efficient energy propagation. Therefore, the respective distances between the carbon nanowires are desirably three times or less as large as the transverse diameter of the gold particle. The required number of carbon nanowires is at least one or more required, but may be determined by the wavelength of surface plasmon excited. When the arrangement of the carbon nanowire group 1A can cover a spatial distance of half the propagation wavelength of the surface plasmon, the effect is increased significantly more than before.

According to the present embodiment, as described previously, the excitation laser light 1E is made incident onto the light entrance slope from the back side of the Si cantilever 1D so as to reach the plasmon resonance angle of 16.12°, thereby making it possible to excite the surface plasmon 1J with the maximum intensity, and thus maximizing the energy propagated to the tip part of the chip 1B. The excitation of the surface plasmon 1J makes it possible to generate the near-field light 1F for measurement with the maximum intensity at the gold filled part 1Q1 of the main carbon nanowire 1Q disposed at the lowermost end of the carbon nanowire group 1A.

Figure 5:
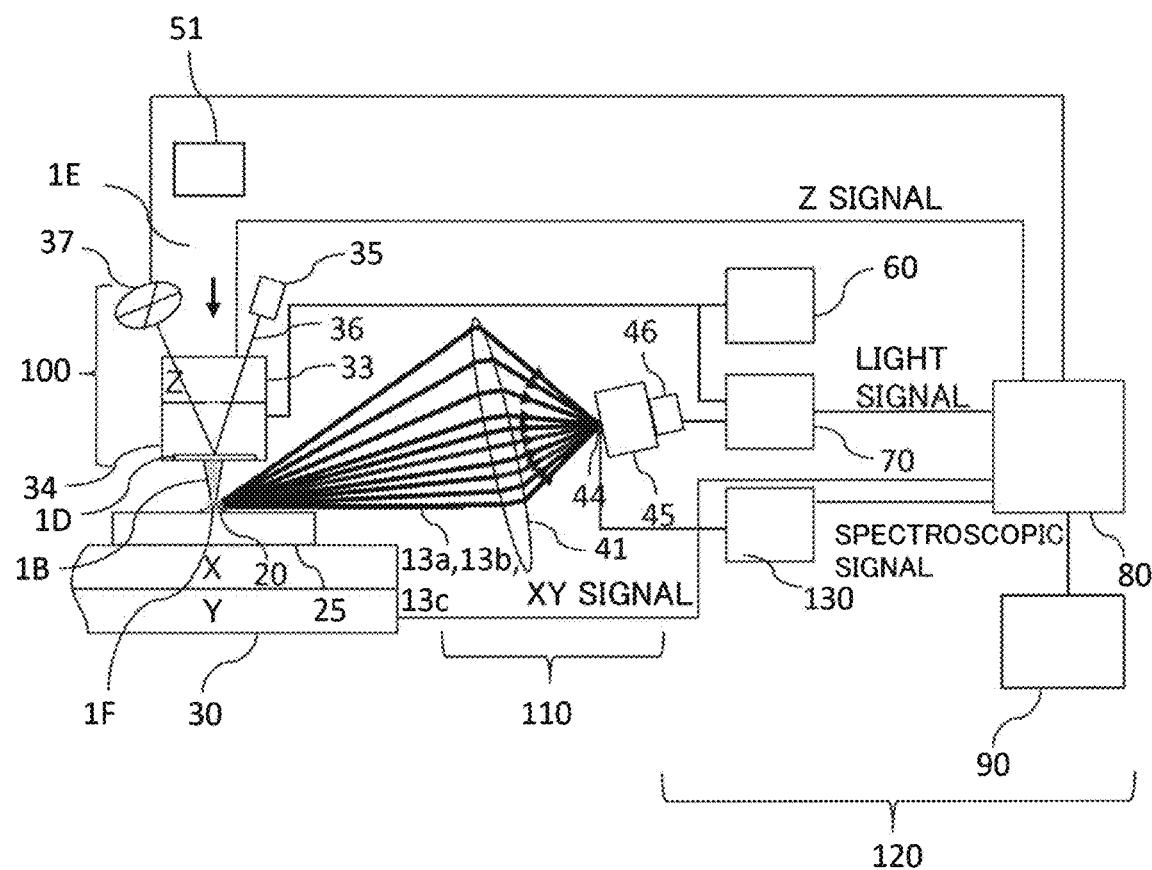
FIG. 5 is a block diagram illustrating a schematic configuration example of a scanning probe microscope according to the first embodiment.

For example, through a simulated calculation, in the case of using the excitation laser light 1F with a wavelength of 850 nm, eight carbon nanowires are required for satisfying the condition for the generation of the near-field light 1F for measurement. When this carbon nanowire group is used, the intensity of the near-field light for measurement can be improved five times or more as much as the near-field light for measurement, generated at the gold filled part 1Q1 when only one gold filled carbon nanowire is used for the tip of the chip 1B. FIG. 5 shows therein a configuration example of a scanning probe microscope based on the principle of generating the above-mentioned near-field light if for measurement.

FIG. 5 is a block diagram illustrating a schematic configuration example of a scanning probe microscope according to the first embodiment. The scanning probe microscope is configured to include a sample holder 25 for mounting a sample 20, an XY piezoelectric element stage 30 with the sample holder 25 placed thereon for scanning the sample 20 in the XY directions relatively with respect to a measurement probe, the Si cantilever 1D mounted with the gold-coated chip 1B with the gold-filled carbon nanowire group 1A fixed to the tip of the chip, a piezoelectric element actuator 34 for micro vibration of the Si cantilever 1D in the Z direction, a Z piezoelectric element stage 33 for scanning the Si cantilever 1D in the Z direction relatively with respect to the sample 20, an optical lever detection system 100 for detecting the contact force between the main carbon nanowire 1Q disposed at the lowermost end of the carbon nanowire group and the sample through the detection of flexure of the cantilever 1D, an excitation laser light irradiation system 51 for irradiating the gold-coated chip 1B with the excitation laser light 1E through the back side of the Si cantilever 1D, a scattered light detection system 110 for collecting light referred to as Raman scattered light 13a to Raman scattered light 13c (hereinafter, the Raman scattered light 13a to the Raman scattered light 13c will not be each specifically mentioned, but referred to as Raman scattered light 13 in the case of giving a collective designation), and applying photoelectric conversion to the light, a spectroscope 130 that can collect the Raman scattered light 13 and separate each Raman spectrum component, and a signal processing/control system 120 for generating a Raman spectrum image as a near-field optical image and a surface irregularity image from the scattered light signals, Raman spectrum components, and XYZ displacement signals obtained.

It is to be noted that the XY piezoelectric element stage 30 and the Z piezoelectric element stage 33 constitute a driving unit for scanning the main carbon nanowire 1Q disposed at the lowermost end of the carbon nanowire group 1A relatively with respect to the sample 20.

The optical lever detection system 100 irradiates the back side of the cantilever 1D with laser light 36 from a semiconductor laser 35, and receives the reflected light at a quartering sensor 37, detects the amount of flexure of the cantilever 1D from the positional change of the reflected light, and further detects the contact force between the main carbon nanowire 1Q and the sample 20 from the amount of flexure.

A control unit 80 in the signal processing/control system 120 executes feedback control of the Z piezoelectric element stage 33 such that the contact force constantly has a preset value.

In the acquisition of the near-field optical image, the gold filled part 1Q1 of the main carbon nanowire 1Q disposed at the lowermost end of the carbon nanowire group 1A is micro-vibrated in the Z direction by the piezoelectric actuator 34 at the resonant frequency of the cantilever 1D, on the basis of a signal from an oscillator 60. Therefore, the intensity of the generated near-field light 1F for measurement and Raman scattered light 13 is also modulated at the same frequency. The Raman scattered light 13 is collected by the action of a collecting lens 41 to one point on a light-receiving surface 44 of a detector 45 such as a photomultiplier tube or a diode, and subjected to photoelectric conversion.

In the acquisition of the Raman spectroscopic image, the gold filled part 1Q1 of the main carbon nanowire 1Q disposed at the lowermost end of the carbon nanowire group 1A can be either micro-vibrated with the resonant frequency described above as well as described above, or kept abeyant at each measurement point on the surface of the sample 20. Scattered light of the near-field light 1F for measurement, generated at the gold filled part 1Q1 of the main carbon nanowire 1Q, is guided to the spectroscope 130, and converted to a spectroscopic spectrum.

The scattered light of the near-field light, converted to the spectroscopic spectrum, is detected as signals, and synchronously detected lock-in amplifier 70 in the signal processing/control system 120, thereby resulting in the output of only the frequency component of the Raman scattered light 13. Of the excitation laser light 1E, background scattered light directly scattered slightly at the surface of the sample 20 is a direct-current component which is not affected by the micro vibration of the cantilever 1D, and thus not included in the output signal of the lock-in amplifier 70. Thus, the scanning probe microscope can selectively detect only the near-field light component, with remaining background noise reduced. In addition, the detection of harmonic components such as the second harmonic and third harmonic of the resonant frequency can further improve the S/N ratios of signals.

The signals of the scattered light obtained from the lock-in amplifier 70 are transmitted to the control unit 80 in the signal processing/control system 120, and combined with XY signals from the XY piezoelectric element stage 30 to generate a near-field optical image, and the image is output to a display 90. At the same time, Z signals from the Z piezoelectric element stage 33 are also combined with the XY signals in the control unit 80 to generate a irregularity image of the sample surface, and the image is output to the display 90.

The signals of the Raman scattered light 13 output from the spectroscope 130 are transmitted to the control unit 80 in the signal processing/control system 120. The control unit 80 combines the signals of the Raman scattered light 13 with signals of XY coordinates from the XY piezoelectric element stage 30 to generate a near-field optical image, and outputs the image to the display 90.

The scanning probe microscope of the first embodiment according to the present invention has been described above. It is to be noted that it is also possible to increase the wavelength of the excitation laser light 1E from a single wavelength to a multiple wavelength according to the first embodiment. In such a case, the use of a spectroscope allows for spectroscopic measurement.

Second Embodiment

Figure 6:
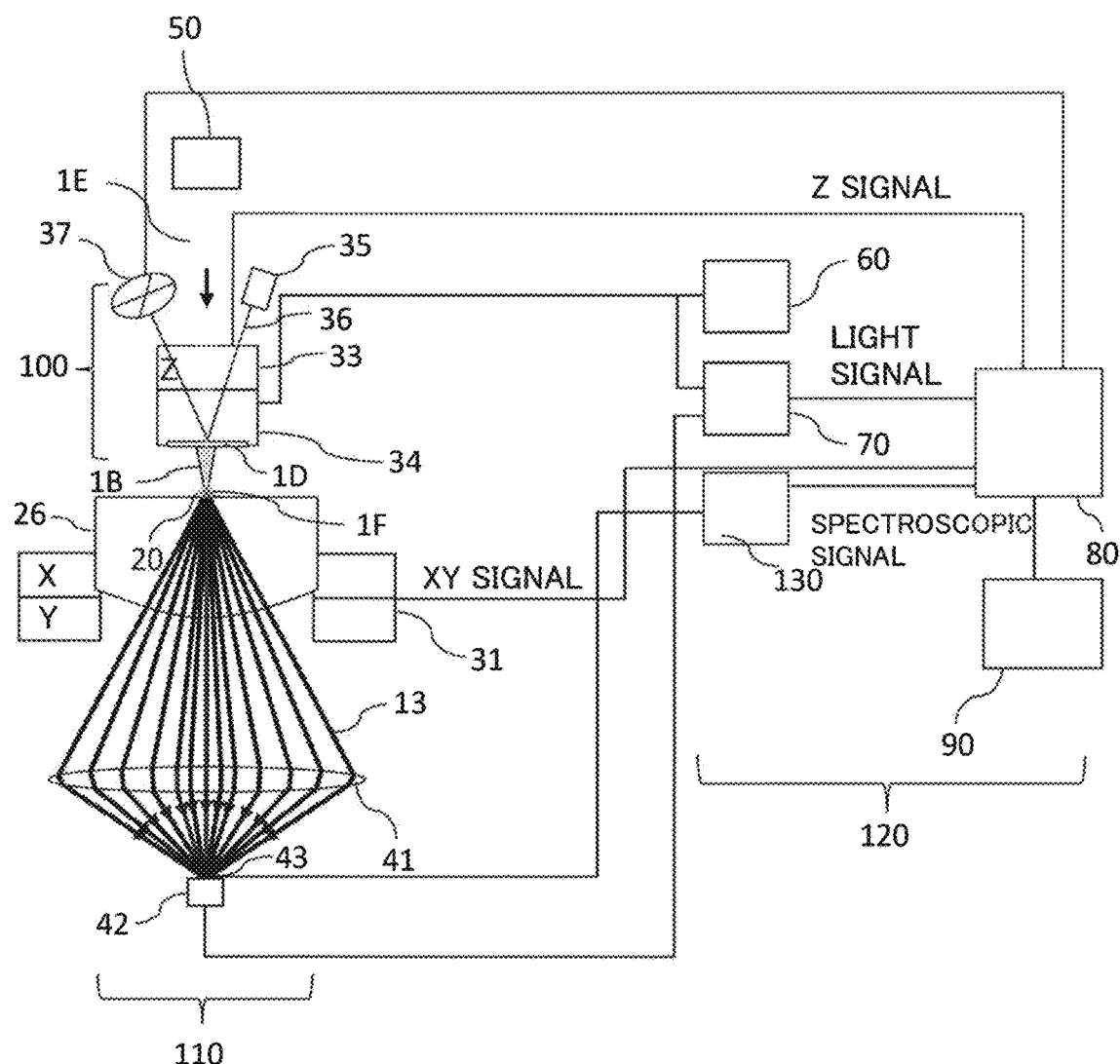
FIG. 6 is a block diagram illustrating a schematic configuration example of a scanning probe microscope according to a second embodiment.

A second embodiment according to the present invention will be described below with reference to FIG. 6. In the scanning with the scanning probe microscope according to the first embodiment, the Raman scattered light 13 at the surface layer of the sample 20 is detected with the near-field light 1F for measurement, emitted from the end of the main carbon nanowire 1Q. According to the second embodiment, Raman scattered light 13 passing through a sample 20 is detected from Raman scattered light 13 of, at the surface layer of the sample 20, near-field light 1F for measurement emitted from an end of a main carbon nanowire 1Q disposed at the lowermost end of a carbon nanowire group 1A.

Specifically, in scanning with the scanning probe microscope according to the second embodiment, the Raman scattered light 13 passing through the sample 20 is collected by a collecting lens 41 to one point on a light-receiving surface 43 of a detector 42 such as a photomultifier tube or a diode, and subjected to photoelectric conversion. Alternatively, the Raman scattered light 13 is collected by the collecting lens 41 to spectroscope 130, and a Raman spectroscopic spectrum is detected. An aperture XY piezoelectric element stage 31 with a sample holder 26 placed therein for scanning the sample 20 in the XY directions has a structure with an aperture in the center where the sample 20 is disposed, because there is a need to allow the passing Raman scattered light 13 to pass through the structure. The other configurations of an excitation laser light irradiation system 50, an optical lever detection system 100, and a signal processing/control system 120, and the other functions are the same as those according to the first embodiment, and description thereof will be thus omitted.

In the second embodiment, there is a need for the measurement sample to be capable of transmitting various types of scattered light (Rayleigh scattering or Raman scattering of excitation light). According to the present embodiment, scattered light is unlikely to be blocked by a Si cantilever 1D, the XY piezoelectric element stage 31, or a Z piezoelectric element stage 33, thus making it possible to achieve a large detecting solid angle, achieve imaging with higher contrast than that in the first embodiment, and further improve the S/N ratio and measurement reproducibility of the near-field optical image.

Third Embodiment

A third embodiment according to the present invention will be described below with reference to FIGS. 7 to 10.

Figure 7:
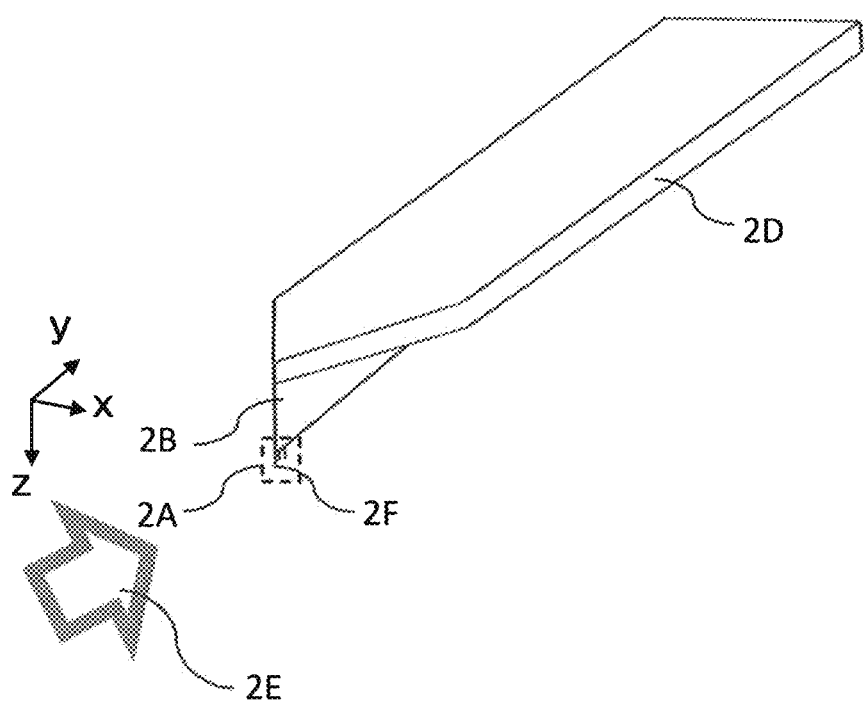
FIG. 7 is a perspective view illustrating an example of a cantilever and an in-depth probe group fixed to a tip of the cantilever according to a third embodiment and a fourth embodiment.

FIG. 7 is a perspective view illustrating an example of a cantilever and an in-depth probe group fixed to a tip of the cantilever according to the third embodiment and a fourth embodiment to be described later. FIG. 7 is a perspective view of a Si cantilever 2D, a chip 2B coated with a noble metal (for example, gold (Au)), formed on the Si cantilever 2D, and a carbon nanowire group 2A (in-depth probe group) fixed to the tip of the chip 2B according to the third embodiment. The chip 2B is formed at the end of the Si cantilever 2D, and the carbon nanowire group 2A composed of a plurality of carbon nanowire s filled with gold is fixed to the chip 2B. The carbon nanowire group 2A is formed by fixing a plurality of carbon nanowires filled with gold in a predetermined arrangement near the tip of the chip 2B.

In this regard, the material of the chip 2B is suitably Si (silicon), but not limited thereto, and may be $SiO_2$ (silicon dioxide), $Si_3N_4$ (silicon nitride), or the like, as long as the material transmits laser light of a specific wavelength. In addition, there may be a noble metal film or a light metal on the surface of the chip 2B, and there may be, for example, a film of gold, aluminum, or silver thereon.

Figure 8:
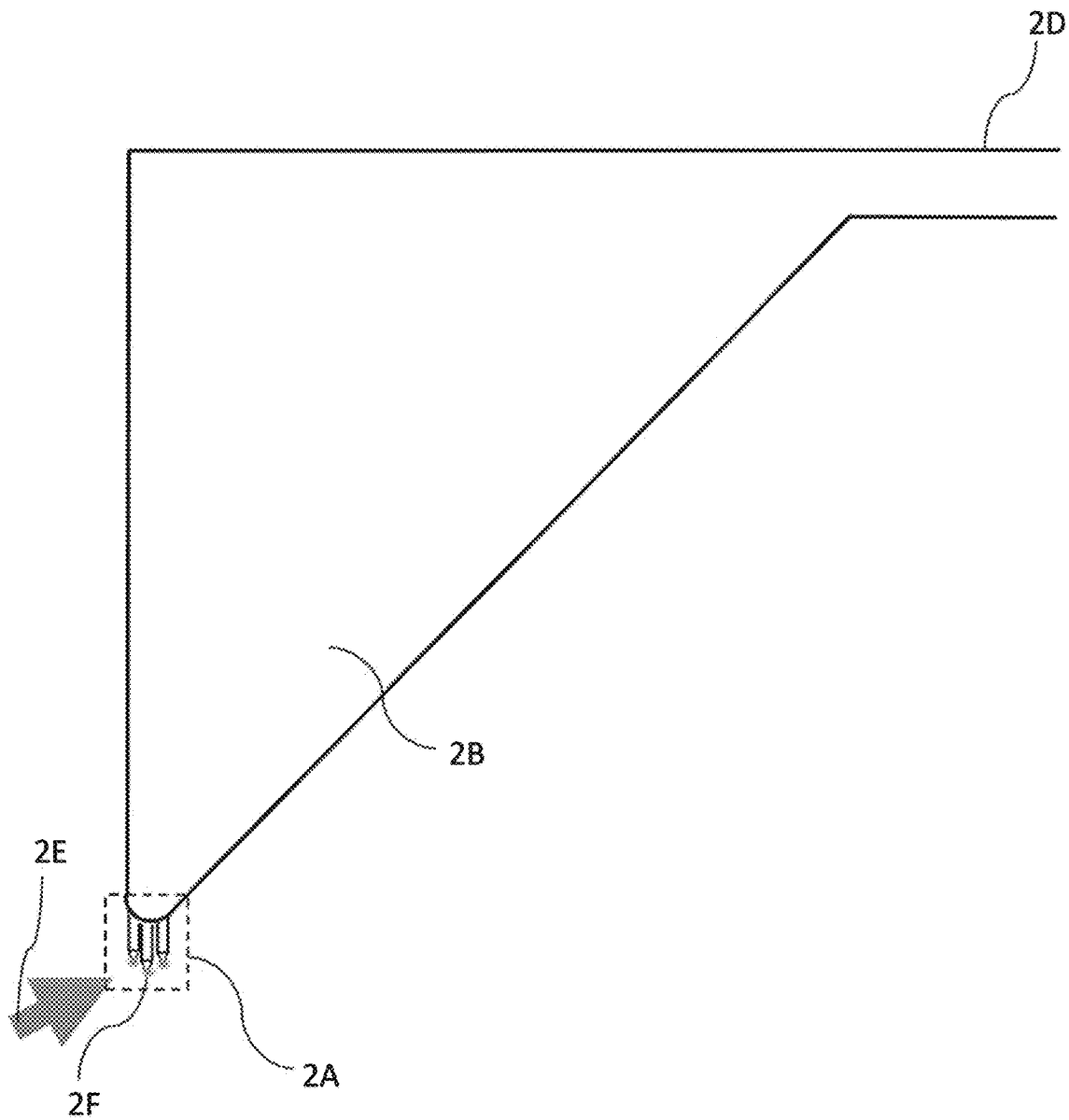
FIG. 8 is a side view illustrating an example of a chip, the in-depth probe group fixed to a tip of the chip, and a light path of excitation laser light in the chip according to the third embodiment through a sixth embodiment.

FIG. 8 is a side view illustrating an example of the chip, the in-depth probe group fixed to the tip of the chip, and a light path of excitation laser light in the chip according to the third embodiment through a sixth embodiment to be described later. As shown in FIG. 8, in the scanning probe microscope according to the third embodiment, the carbon nanowire group 2A at the tip part of the chip 2B is irradiated with excitation laser light 2E. In this regard, the irradiation with the excitation laser light 2E generates local electric field concentration on the metal particles filling each carbon nanowire, thereby generating near-field light 2F for measurement around the individual gold particles.

Figure 9:
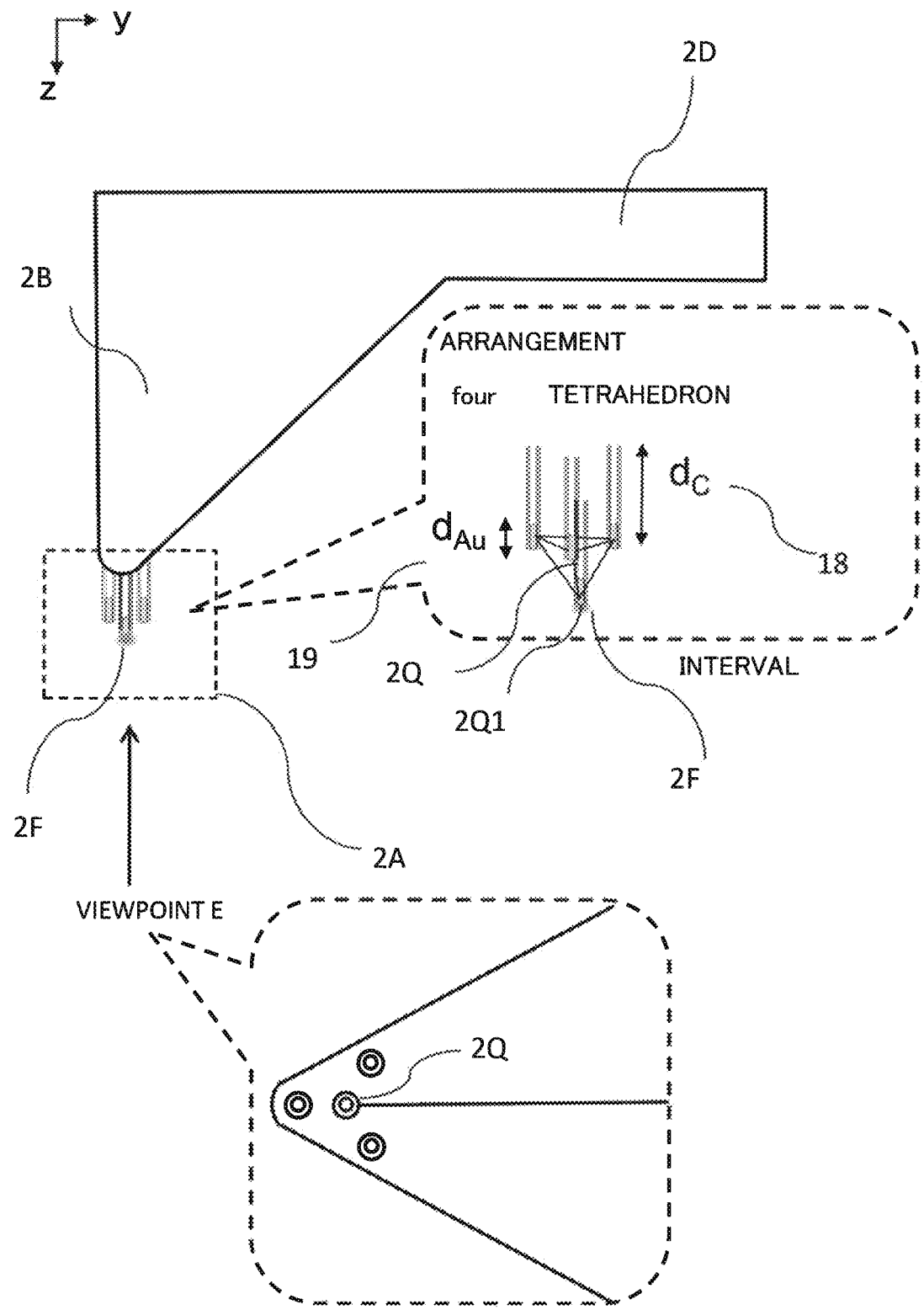
FIG. 9 is a side view illustrating an arrangement example of a carbon wire probe group according to the third embodiment to the sixth embodiment.

FIG. 9 is a side view illustrating an arrangement example of a carbon wire probe group according to the third embodiment to the sixth embodiment to be described later. In order to a high measurement resolution, one main carbon nanowire 2Q of the carbon nanowire group 2A, which is disposed at the lowermost end, is responsible for the emission of the near-field light 2F for measurement, thereby determining the measurement resolution. The other carbon nanowires of the carbon nanowire group 2A, other than the main carbon nanowire 2Q, surrounds, as auxiliary carbon nanowires, the main carbon nanowire 2Q in a predetermined arrangement around the main carbon nanowire 2Q. The auxiliary carbon nanowires have ends provided at predetermined distances from the chip 2B, and the main carbon nanowire 29 has an end provided at a distance equal to or longer than the distance from the chip to the end of the auxiliary carbon nanowire. More specifically, the main carbon nanowire 2Q desirably has an end protruded more than the auxiliary carbon nanowires. The respective carbon nanowires filled with gold, which constitute the noble-metal carbon nanowire group 2A, can be fixed by a method such as sputtering to the tip of the chip 2B in predetermined locations.

The length $d_c$ 18 of the main carbon nanowire 2Q is about 50 to 100 nm. The filling metal particles are vertically long, and the length $d_{Au}$ 19 of the metal particle is 10 to 30 nm. The transverse diameter corresponds to the inside diameter of the carbon nanowire, which is 5 to 10 nm. The effective size of the near field obtained by electric field concentration corresponds to 1 to 2 times as large as the diameter of the metal particle, and the distances between the carbon nanowires are thus desirably three times or less as large as the transverse diameter of the gold particle, such that the near field around the gold particles filling the ends of the respective auxiliary carbon nanowires arranged around the main carbon nanowire 2Q disposed at the lowermost end can enhance the near field generated by the gold particles filling the end of the main carbon nanowire 2Q disposed at the lowermost end. The required number of carbon nanowires is basically two or more required. Desirably, efficiently, regardless of the incident direction of the excitation laser light 2E, as in the figure from a viewpoint E of looking up the cantilever 2D from underneath as shown in FIG. 9, such an arrangement that constitutes a symmetrical tetrahedron is desirable where the center is protruded to serve as the main carbon nanowire 2Q disposed at the lowermost end when the end of the gold particles is considered as a vertex. In the case of a tetrahedral arrangement, it has been found that the intensity of the generated near-field light 2F for measurement is significantly increased at a gold filled part 2Q1 of the main carbon nanowire 2Q disposed at the lowest end.

Figure 10:
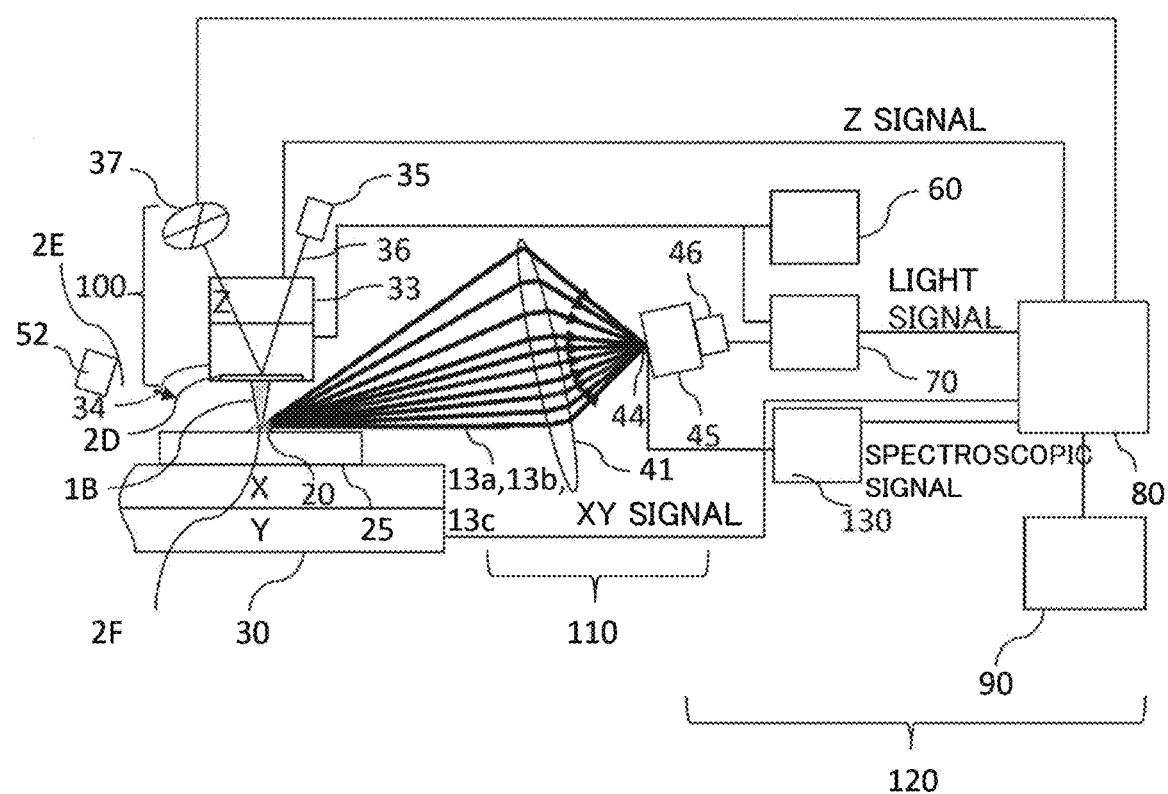
FIG. 10 is a block diagram illustrating a schematic configuration example of a scanning probe microscope according to the third embodiment.

According to the third embodiment, the excitation laser light 2E is made incident onto the end of the cantilever 2D, thereby making it possible to generate the intense near-field light 2F for measurement. For example, according to a simulated calculation, it has been confirmed that when four carbon nanowires are arranged to make a regular tetrahedron with the use of the excitation laser light 2E of 850 nm in wavelength, the intensity of the near-field light 2F for measurement is improved five times or more as much as compared with a case where only one main carbon nanowire 2Q is disposed at the tip of the chip 2B. FIG. 10 shows the configuration of a scanning probe microscope according to the third embodiment.

FIG. 10 is a block diagram illustrating a schematic configuration example of the scanning probe microscope according to the third embodiment. The scanning probe microscope according to the third embodiment is basically configured in the same manner as in the first embodiment, but irradiation of the chip 2B with the excitation laser light 2E from a side surface of the Si cantilever 2D, that is, an excitation laser light irradiation system 52 differs from the excitation laser light irradiation system 51 according to the first embodiment.

This configuration can increase the intensity of the near-field light 2F for measurement. In addition, the degree of freedom for the placement of the excitation laser light irradiation system 52 can be considered capable of being increased. The other configuration is the same as that according to the first embodiment, and description thereof will be thus omitted. In addition, also in the third embodiment, the use of a spectroscope makes also it possible to increase the wavelength of the excitation laser light 25 from a single wavelength to a multiple wavelength.

Fourth Embodiment

A fourth embodiment according to the present invention will be described below with reference to FIG. 11.

Figure 11:
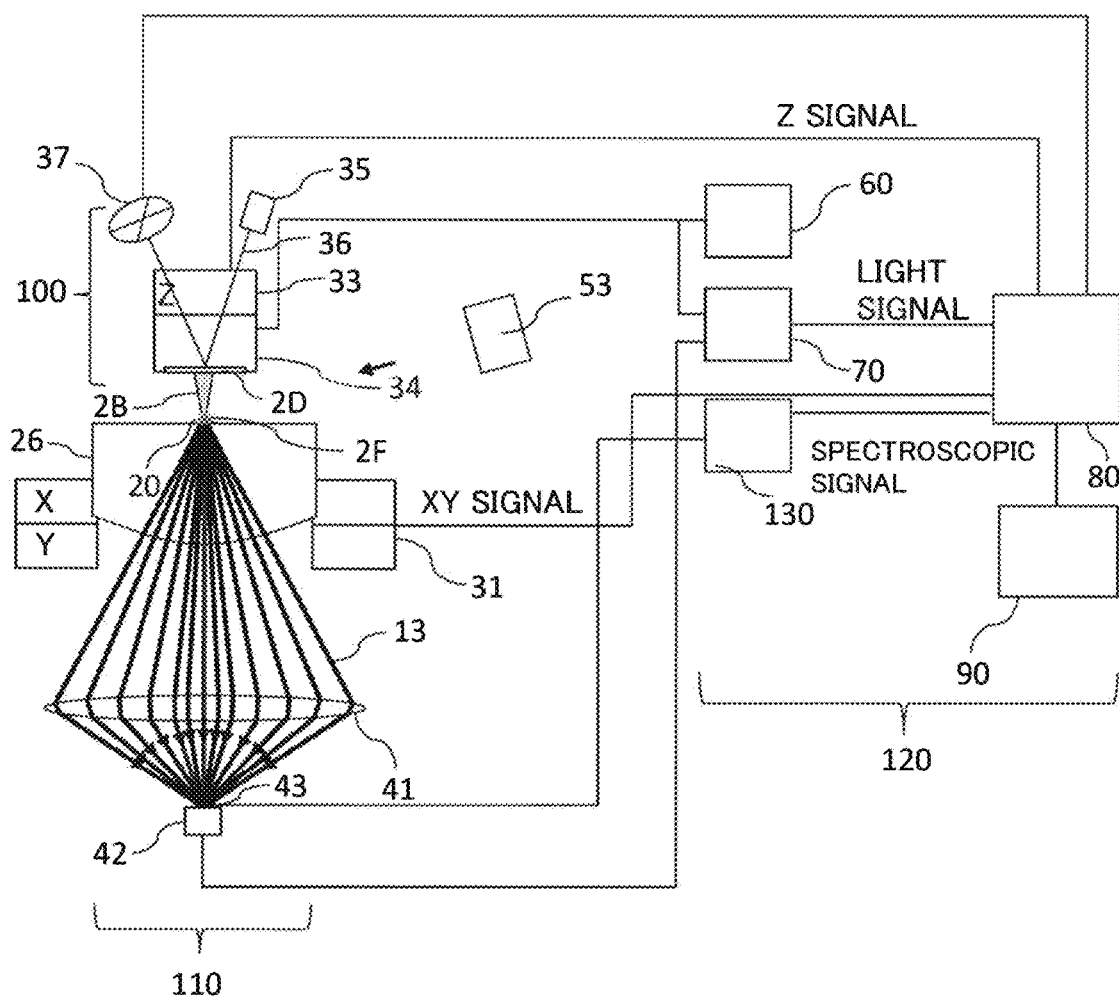
FIG. 11 is a block diagram illustrating a schematic configuration example of a scanning probe microscope according to the fourth embodiment.

FIG. 11 is a block diagram illustrating a schematic configuration example of a scanning probe microscope according to the fourth embodiment. According to the third embodiment, Raman scattered light 13 at the surface layer of a sample 20 is detected through the irradiation with the near-field light 2F for measurement, emitted from the end of the main carbon nanowire 2Q. However, according to the fourth embodiment, through irradiation with near-field light 2F for measurement, emitted from an end of a main carbon nanowire 2Q disposed at the lowermost end of a carbon nanowire group 2A, Raman scattered light 13 passing through a sample 20 is detected from Raman scattered light at the surface layer of the sample 20.

Specifically, in scanning with the scanning probe microscope according to the fourth embodiment, the Raman scattered light 13 passing through the sample 20 is collected by a collecting lens 41 to one point on a light-receiving surface 43 of a detector 42 such as a photomultiplier tube or a diode, and subjected to photoelectric conversion. Alternatively, the Raman scattered light 13 is collected by the collecting lens 41 to a spectroscope 130, and a Raman spectroscopic spectrum is detected. An aperture XY piezoelectric element stage 31 with a sample holder 26 placed therein for scanning the sample 20 in the XY directions has a structure with an aperture in the center where the sample 20 is disposed, because there is a need to allow the passing Raman scattered light 13 to pass through the structure. The other configurations of an excitation laser light irradiation system 53, an optical lever detection system 100, and a signal processing/control system 120, and the other functions are the same as those according to the third embodiment, and description thereof will be thus omitted.

In the fourth embodiment, there is a need for the measurement sample to be capable of transmitting various types of scattered light (Rayleigh scattering or Raman scattering of excitation light). According to the present embodiment, scattered light is unlikely to be blocked by a Si cantilever 2D, the aperture XY piezoelectric element stage 31, or a Z piezoelectric element stage 33, thus making it possible to achieve a large detecting solid angle, achieve imaging with higher contrast than that in the first embodiment, and further improve the S/N ratio and measurement reproducibility of the near-field optical image.

Fifth Embodiment

A fifth embodiment according to the present invention will be described below with reference to FIG. 12.

Figure 12:
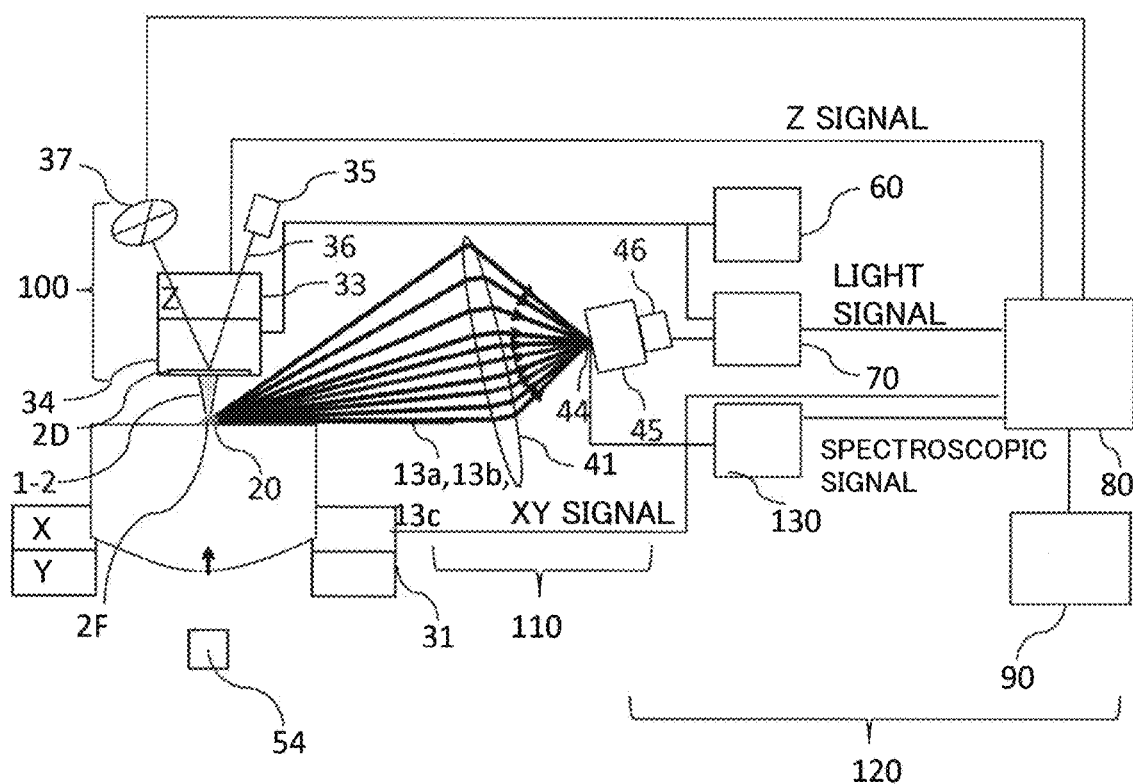
FIG. 12 is a block diagram illustrating a schematic configuration example of a scanning probe microscope according to the fifth embodiment.

FIG. 12 is a block diagram illustrating a schematic configuration example of a scanning probe microscope according to the fifth embodiment. The scanning probe microscope according to the fifth embodiment is basically configured in the same manner as in the third embodiment, but irradiation of a chip 2B with excitation laser light 2E from underneath a Si cantilever 2D, that is, an excitation laser light irradiation system 54 differs from the excitation laser light irradiation system 52 according to the third embodiment.

In the fifth embodiment, there is a need for the measurement sample to be capable of transmitting various types of scattered light (Rayleigh scattering or Raman scattering of excitation light). According to the fifth embodiment, scattered light is unlikely to be blocked by the Si cantilever 2D, an aperture XY piezoelectric element stage 31, or a Z piezoelectric element stage 33, thus making it possible to achieve a large detecting solid angle, achieve imaging with higher contrast than that in the first embodiment, and further improve the S/N ratio and measurement reproducibility of the near-field optical image.

This configuration can be considered capable of increasing the degree of freedom for the placement of the excitation laser light irradiation system 54. The other configuration is the same as that according to the third embodiment, and description thereof will be thus omitted. In addition, also in the fifth embodiment, the use of a spectroscope makes it possible to increase the wavelength of excitation laser light 2E from a single wavelength to a multiple wavelength.

[Sixth Embodiment]

A sixth embodiment according to the present invention will be described below with reference to FIG. 13.

Figure 13:
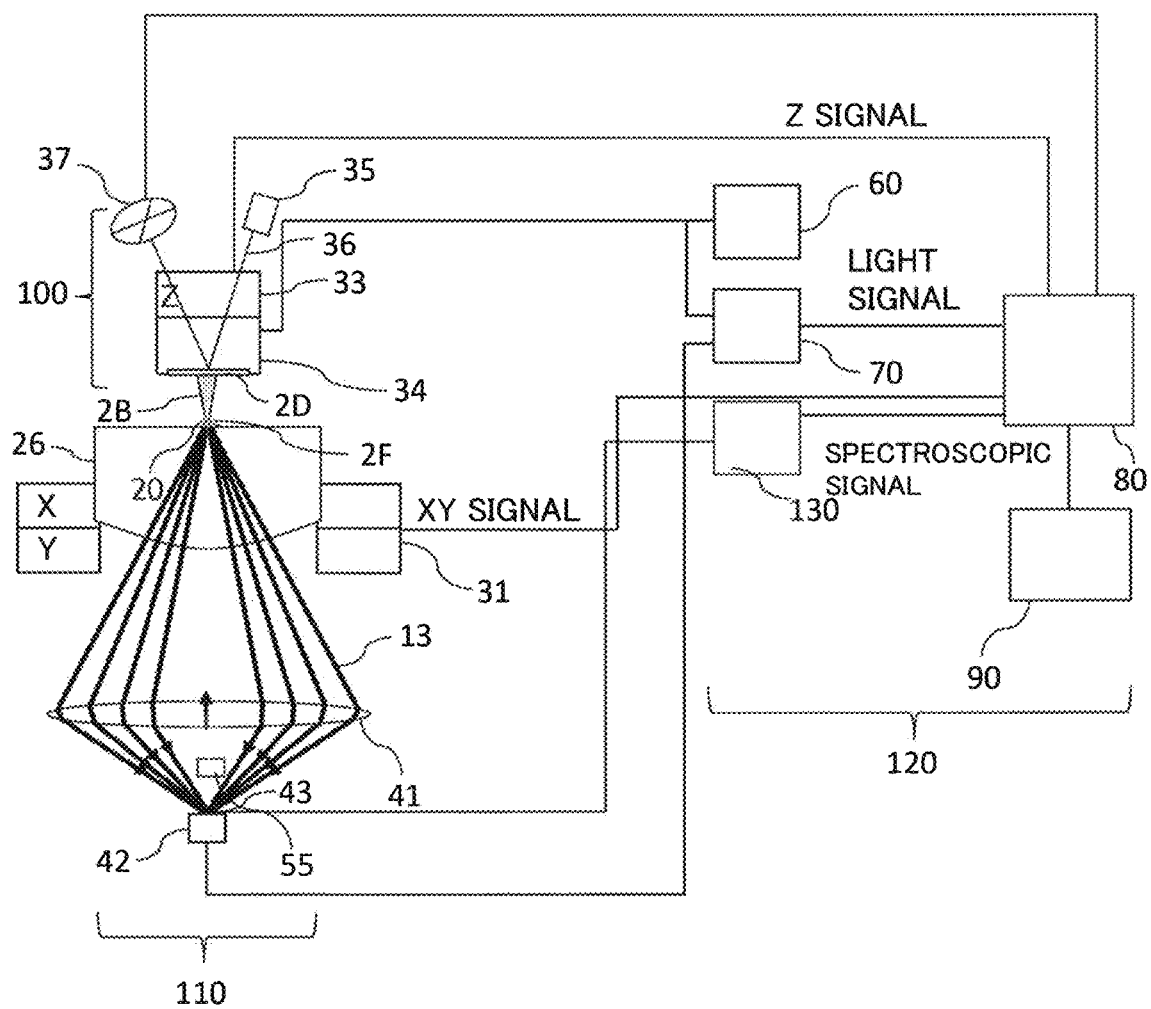
FIG. 13 is a block diagram illustrating a schematic configuration example of a scanning probe microscope according to the sixth embodiment.

FIG. 13 is a block diagram illustrating a schematic configuration example of a scanning probe microscope according to the sixth embodiment. The scanning probe microscope according to the sixth embodiment is basically configured in the same manner as in the fifth embodiment, but while Raman scattered light 13 of, at the surface layer of a sample 20, near-field light 2F for measurement at an end of a main carbon nanowire 2Q is detected according to the fifth embodiment, scattered light passing through a sample 20 is detected further below an excitation laser light irradiation system 55, from scattered light of, at the surface layer of the sample 20, near-field light 2F for measurement, emitted from an end of a main carbon nanowire 2Q disposed at the lowermost end of a carbon nanowire group 2A, according to the sixth embodiment.

Specifically, the Raman scattered light 13 is collected by a collecting lens 41 disposed further below the excitation laser light irradiation system 55, to one point on a light-receiving surface 43 of a detector 42 such as a photomultiplier tube or a diode, and subjected to photoelectric conversion. Alternatively, the Raman scattered light 13 is collected by the collecting lens 41 to a spectroscope 130, and a Raman spectroscopic spectrum is detected. An aperture XY piezoelectric element stage 31 with a sample holder 26 placed therein for scanning the sample 20 in the XY directions has a structure with an aperture in the center where the sample 20 is disposed, because there is a need to allow the passing Raman scattered light 13 to pass through the structure. The other configurations of the excitation laser light irradiation system 55, an optical lever detection system 100, and a signal processing/control system 120, and the other functions are the same as those according to the fifth embodiment, and description thereof will be thus omitted.

In the sixth embodiment, there is a need for the measurement sample to be capable of transmitting various types of scattered light (Rayleigh scattering or Raman scattering of excitation light). According to the sixth embodiment, scattered light is unlikely to be blocked by a Si cantilever 2D, the aperture XY piezoelectric element stage 31, or a Z piezoelectric element stage 33, thus making it possible to achieve a large detecting solid angle, achieve imaging with higher contrast than that in the first embodiment, and further improve the S/N ratio and measurement reproducibility of the near-field optical image.

The embodiments mentioned above have been described in detail for clearly explaining the present invention, but are not necessarily to be considered limited to the inclusion of all of the configurations described. It is possible to replace a part of a configuration according to an embodiment with another configuration, and in addition, it is also possible to add a configuration according to an embodiment to a configuration according to another embodiment. In addition, it is also possible to remove a part of a configuration according to an embodiment.

In addition, the respective parts, configurations, functions, processing units, etc. mentioned above may be partially or entirely achieved with hardware, for example, by designing with integrated circuits. In addition, the respective parts, configurations, functions, etc. mentioned above may be achieved with software in a way that a processor interprets and executes programs for achieving the respective functions. Information such as programs, tables, and files for achieving the respective functions can be stored on recording devices such as memories and hard disks, or recording media such as IC cards, SD cards, and DVDs.

It is to be noted that the control lines and information lines according to the embodiments described above are shown which are considered required for the sake of explanation, but all of the control lines and information lines required for a product are not always shown. In fact, it is conceivable that almost all of the configurations are interconnected. The present invention has been described above mainly with respect to the embodiments.

What is claimed is:

1. A near-field scanning probe microscope comprising:
    a measurement probe configured to relatively scan a test sample;
    an excitation light irradiation system;
    a near-field light generation system configured to generate near-field light in a region comprising the measurement probe in response to irradiation with excitation light from the excitation light irradiation system; and
    a scattered light detection system configured to detect Rayleigh scattering and Ramen scattered light of the near-field light from the sample, generated between the measurement probe and the sample,
    wherein the near-field light generation system comprises a cantilever with a chip coated with a noble metal, and a tip of the chip is provided with a nanowire wire group comprising a plurality of carbon nanowires with a noble metal provided at ends thereof; and
    wherein the nanowire wire group comprises a main carbon nanowire for measurement, the main carbon nanowire being the carbon nanowire closest to the sample and being used to determine a measurement resolution, and adjacent to the main carbon nanowire, a plurality of auxiliary carbon nanowires is disposed in a predetermined arrangement to act as an antenna.

2. The near-field scanning probe microscope according to claim 1,
    wherein the auxiliary carbon nanowires are provided to have ends located at a first distance from the chip, and the main carbon nanowire is provided to have an end located at a second distance that is equal to or longer than the first distance.

3. The near-field scanning probe microscope according to claim 1,
    wherein the carbon nanowires are about 50 to 100 nm (nanometers) in length,
    particles of the filling noble metal are 10 to 30 nm in longitudinal diameter,
    transverse diameters of the particles of the filling noble metal correspond to inside diameters of the carbon nanowires, and a distance between the carbon nanowires is three times or less as large as the transverse diameters of the particles of the filling noble metal.

4. The near-field scanning probe microscope according to claim 1,
wherein the auxiliary carbon nanowires are provided to have ends located at a first distance from the chip,
the main carbon nanowire is provided to have an end located at a second distance that is equal to or longer than the first distance from the chip, and
the ends of the auxiliary carbon nanowires are provided to have a centrosymmetry with respect to the end of the main carbon nanowire.

5. The near-field scanning probe microscope according to claim 1,
wherein the auxiliary carbon nanowires are provided to have ends located at a first distance from the chip,
the main carbon nanowire is provided to have an end located at a second distance that is equal to or longer than the first distance from the chip, and
the ends of the auxiliary carbon nanowires are provided to constitute a tetrahedron with the end of the main carbon nanowire as a vertex.

6. The near-field scanning probe microscope according to claim 1,
wherein the auxiliary carbon nanowires are provided to have ends located at a first distance from the chip,
the main carbon nanowire is provided to have an end located at a second distance that is equal to or longer than the first distance from the chip, and
the ends of the auxiliary carbon nanowires are provided to have a centrosymmetry with respect to the end of the main carbon nanowire, and
the near-field light generation system irradiates the tip of the chip with the excitation light, thereby generating electric field concentration on the noble metal at the ends of the carbon nanowires, and thus generating the near-field light.

7. The near-field scanning probe microscope according to claim 1,
wherein the auxiliary carbon nanowires are provided to have ends located at a first distance from the chip,
the main carbon nanowire is provided to have an end located at a second distance that is equal to or longer than the first distance from the chip, and
the ends of the auxiliary carbon nanowires are provided linearly to include the end of the main carbon nanowire as an end point.

8. The near-field scanning probe microscope according to claim 1,
wherein the auxiliary carbon nanowires are provided to have ends located at a first distance from the chip,
the main carbon nanowire is provided to have an end located at a second distance that is equal to or longer than the first distance from the chip,
the ends of the auxiliary carbon nanowires are provided linearly to include the end of the main carbon nanowire as an end point, and
the near-field light generation system makes the excitation light incident onto an interface between the noble metal coating the chip and the cantilever to make a plasmon resonance angle, thereby generating electric field concentration on the noble metal at the ends of the carbon nanowires, and thus generating the near-field light.

9. A probe for a scanning probe microscope, the probe comprising:
a supporting member;
a chip provided on the supporting member; and
a nanowire wire group comprising a plurality of carbon nanowires provided at a tip of the chip,
wherein the chip is coated with a noble metal,
the carbon nanowires are each provided, on an end thereof, with a noble metal,
wherein the supporting member transmits energy of a predetermined wavelength,
the supporting member has a surface at least partially covered with a predetermined noble metal that blocks the energy of the predetermined wavelength, and
when an interface between the supporting member and the predetermined noble metal is irradiated with excitation light with the predetermined wavelength passing through the supporting member so as to make a plasmon resonance angle, plasmon is propagated to the nanowire wire group, thereby generating local electric field concentration on the noble metal at ends of the carbon nanowires.

10. A sample observation method of using a scanning probe microscope comprising:
a measurement probe configured to relatively scan a test sample;
an excitation light irradiation system;
a near-field light generation system configured to generate near-field light in a region comprising the measurement probe in response to irradiation with excitation light from the excitation light irradiation system; and
a scattered light detection system configured to detect Rayleigh scattering and Ramen scattered light of the near-field light from the sample, generated between the measurement probe and the sample,
wherein the near-field light generation system comprises a cantilever with a chip coated with a noble metal, and
a tip of the chip is provided with a nanowire wire group comprising a plurality of carbon nanowires with a noble metal provided at ends thereof,
the method of implementing:
a procedure of generating excitation near-field light in the nanowire wire group in response to energy given by the excitation light;
a scattered light detection procedure of detecting Rayleigh scattering and Ramen scattered light of the near-field light from the sample, generated between the measurement probe and the sample;
an irradiation procedure of making the excitation light incident at a plasmon resonance angle onto an interface between the noble metal coating the chip and the chip by passing the excitation light through the chip;
a propagation procedure of propagating plasmon to the carbon nanowire group at the tip of the chip; and
an electric field concentration procedure of generating local electric field concentration on the noble metal provided on the respective carbon nanowires.

11. The sample observation method according to claim 10,
wherein the procedure of generating the near-field light implements, with the scanning probe microscope,
an irradiation procedure of irradiating the tip of the chip with the excitation light, and
an electric field concentration procedure of generating local electric field concentration on the noble metal provided on the carbon nanowires in accordance with the irradiation procedure.

12. The probe according to claim 9, wherein the nanowire wire group comprises a main carbon nanowire for measurement, the main carbon nanowire being the carbon nanowire closest to the sample and being used to determine a measurement resolution, and adjacent to the main carbon nanowire, a plurality of auxiliary carbon nanowires is disposed in a predetermined arrangement to act as an antenna.

13. The probe according to claim 12, wherein the auxiliary carbon nanowires are provided to have ends located at a first distance from the chip,
the main carbon nanowire is provided to have an end located at a second distance that is equal to or longer than the first distance from the chip, and
the ends of the auxiliary carbon nanowires are provided linearly to include the end of the main carbon nanowire as an end point.

14. The probe according to claim 9, wherein
the carbon nanowires are about 50 to 100 nm (nanometers) in length,
particles of the noble metal are 10 to 30 nm in longitudinal diameter,
transverse diameters of the particles of the noble metal correspond to inside diameters of the carbon nanowires, and
a distance between the carbon nanowires is three times or less as large as the transverse diameters of the particles of the noble metal.

15. The probe according to claim 12, wherein
the auxiliary carbon nanowires are provided to have ends located at a first distance from the chip,
the main carbon nanowire is provided to have an end located at a second distance that is equal to or longer than the first distance from the chip, and
the ends of the auxiliary carbon nanowires are provided to have a centrosymmetry with respect to the end of the main carbon nanowire.

16. The probe according to claim 12, wherein
the auxiliary carbon nanowires are provided to have ends located at a first distance from the chip,
the main carbon nanowire is provided to have an end located at a second distance that is equal to or longer than the first distance from the chip, and
the ends of the auxiliary carbon nanowires are provided to constitute a tetrahedron with the end of the main carbon nanowire as a vertex.

\* \* \* \* \*